United States Patent
Grottini (10) Patent No.: US 11,952,262 B2
(45) Date of Patent: Apr. 9, 2024

(54) BEVERAGE DISPENSER WITH CONTAINER WASHING SYSTEM

(71) Applicant: BLUPURA S.R.L, Cadriano di Granarolo dell'Emilia (IT)

(72) Inventor: Gianni Grottini, Porto Recanati (IT)

(73) Assignee: Blupura S.R.L., Cadriano di Granarolo del'Emila (IT)

( * ) Notice: Subject to any disclaimer, the term of this patent is extended or adjusted under 35 U.S.C. 154(b) by 0 days.

(21) Appl. No.: 18/012,002

(22) PCT Filed: Jul. 7, 2021

(86) PCT No.: PCT/IB2021/056098
§ 371 (c)(1),
(2) Date: Dec. 21, 2022

(87) PCT Pub. No.: WO2022/023844
PCT Pub. Date: Feb. 3, 2022

(65) Prior Publication Data
US 2023/0264943 A1    Aug. 24, 2023

(30) Foreign Application Priority Data
Jul. 31, 2020   (IT) .................. 102020000018697

(51) Int. Cl.
*A61L 2/18* (2006.01)
*B67D 7/02* (2010.01)
*B67D 7/84* (2010.01)
(52) U.S. Cl.
CPC .............. *B67D 7/84* (2013.01); *A61L 2/183* (2013.01); *B67D 7/02* (2013.01); *A61L 2202/23* (2013.01); *B67D 2210/00078* (2013.01)

(58) Field of Classification Search
CPC .. B67D 7/84; B67D 7/02; B67D 2210/00078; B67D 2210/00023; B67D 3/00; A61L 2/183; A61L 2202/23; B65B 55/00
(Continued)

(56) References Cited

U.S. PATENT DOCUMENTS

| 5,443,739 | A  | * | 8/1995  | Vogel  | B08B 9/0826 210/257.2 |
| 9,550,662 | B1 | * | 1/2017  | Brown  | B67D 7/348 |
| 2004/0208781 | A1 | * | 10/2004 | Hayashi | B67C 7/0073 422/302 |

FOREIGN PATENT DOCUMENTS

| GB | 2271048 | 4/1994 |
| GB | 2462319 | 2/2010 |
(Continued)

*Primary Examiner* — Jason K Niesz
(74) *Attorney, Agent, or Firm* — Shalom Wertsberger; Saltamar Innovations (57) ABSTRACT

Dispenser (10), for the dispensing of drinking water and/or other beverages, comprising: —a cabinet (100); —a user interface (112); —a dispensing compartment (113) having a support surface (1130) for a container (9) to be filled; —at least one nozzle (114) for the dispensing of drinking water and/or other beverages, positioned over said support surface (1130); —a washing compartment (1) for said container (9), said washing compartment (1) comprising: —a washing device for dispensing one or more washing fluids inside said container (9), —a drain (60) for draining one or more washing fluids outside said washing compartment (1), wherein said washing compartment (1) for said container (9) comprises: a basket (11) adapted to contain said container (9) to be washed in an upside down setup, said basket (11) being movable between: —a first operating position, wherein said basket (11) is completely inserted inside said washing compartment (1) to enable to wash the container (9) contained therein, —and a second operating position,
(Continued)

wherein said basket (11) projects, at least partially, from said washing compartment (1) to enable to insert said container (9) to be washed and pull it out once the washing operations are concluded, said washing device being adapted to provide, alternatively, water and water plus ozone when said basket (11) is located in said first operating position.

15 Claims, 5 Drawing Sheets (58) Field of Classification Search
USPC .................................................. 141/85, 89
See application file for complete search history.

(56) References Cited

FOREIGN PATENT DOCUMENTS

| | | |
|---|---|---|
| JP | 2003317144 | 11/2003 |
| WO | WO94/06547 | 3/1994 |

* cited by examiner

BEVERAGE DISPENSER WITH CONTAINER WASHING SYSTEM

A device for supplying drinking water and/or beverages in general is described below, having a system for washing and sanitizing the container designed to contain the beverage dispensed.

Known dispensers (hereinafter, said term will be used to identify a generic "device for dispensing water and/or beverages") designed for use in workplaces, restaurants and public places and/or outdoors.

Dispensers of this kind are described, for example, in the European patent EP3049364 of the same applicant of this patent application.

Typically a dispenser provides for the connection to the water mains and/or storage tanks of the beverage to be dispensed, and is designed to supply drinking water and/or beverages (after purification, where necessary, with known filters and/or debacterizing units) at room temperature and/or refrigerated (by known refrigerating means) and/or carbonated (by adding carbon dioxide).

The dispenser is then equipped with at least one dispensing station to access the beverage dispensing nozzle, under which to position the container to be filled, as well as special start-up commands for the dispensing function, typically comprising at least one currency acceptance device (or suitable pre-loaded card or key with micro-chip) and at least one interface designed to select the operating functions of the dispenser, such as the type of beverage dispensed and related quantity.

Currently known dispensers still have some drawbacks.

The purpose of this invention is to solve, at least in part, the problems of known technique.

In particular, a purpose of the invention is to propose a dispenser that allows guaranteeing adequate hygienic conditions for consumers, with particular reference to the conditions of the container intended to contain the drink dispensed.

Another purpose of the invention is to propose a dispenser the features of which favour ergonomic use for the user.

A possible form of realization of this invention is described below with reference to the drawings annexed in which.

The features of the invention are now described, with the references contained in the figures and with particular reference to the variants represented therein.

It is also specified that any dimensional and spatial term (such as "lower", "upper", "internal", "external", "front", "rear" and the like) refers to the position according to which the elements of the invention are illustrated in the figures annexed, without any intention of limiting the possible operating conditions.

With reference to the drawing tables annexed, reference number 10 indicates, as a whole, a device for dispensing drinking water and/or other beverages, hereinafter abbreviated as "dispenser 10".

Figure 1:
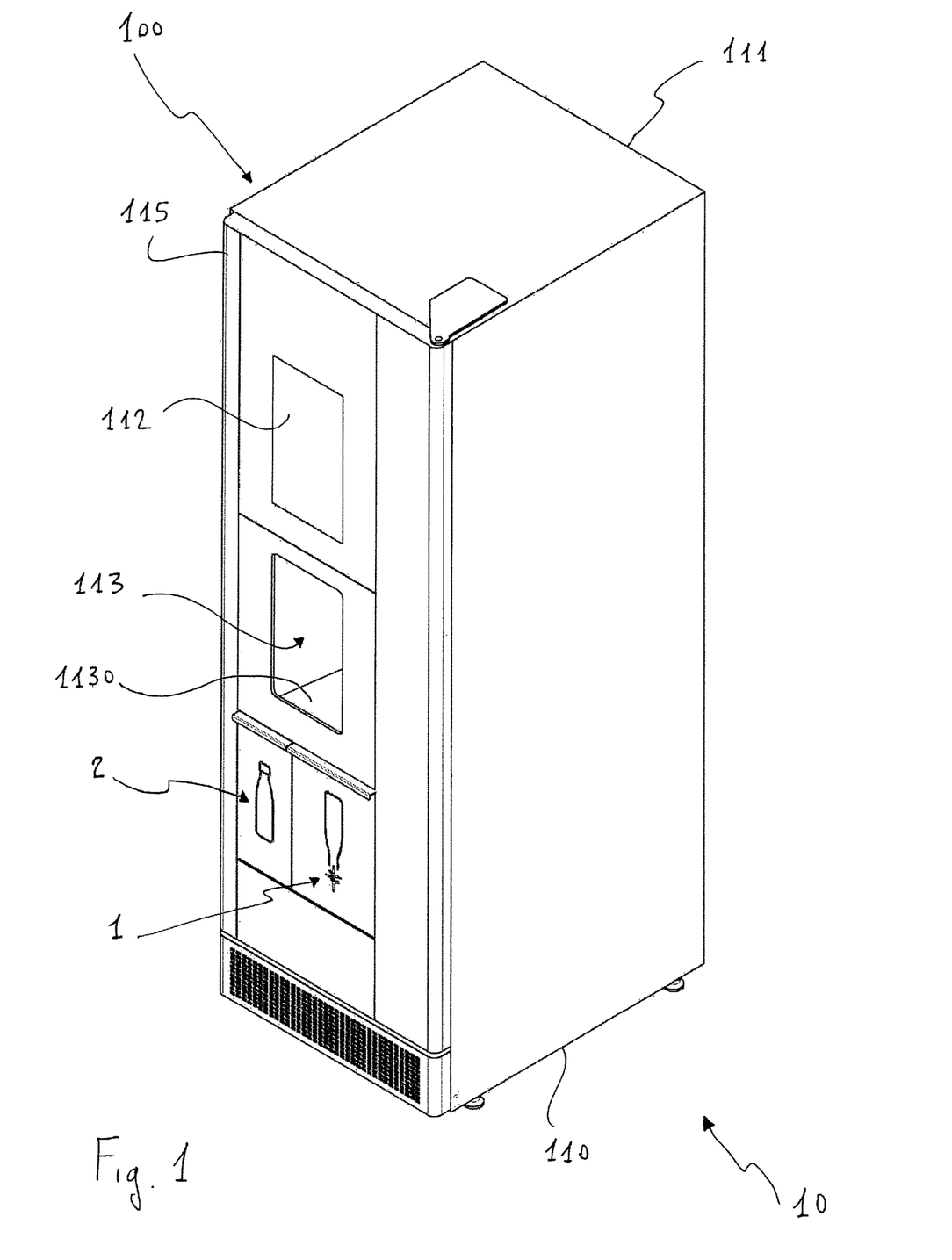
FIG. 1 is a perspective view of the dispenser for dispensing drinking water and/or other beverage according to the invention.

The dispenser 10 comprises a containment and support cabinet 100, having a support base 110 and a top 111; in the example illustrated, the cabinet 100 has a substantially and/or essentially polygonal cross section, for example quadrangular. However, said cabinet 100 can have the most varied architectural and dimensional configurations, in consideration of the intended context and the needs inherent in the type of use.

Said cabinet 100 defines an internal volume designed to house the classic constructive-functional components of a dispenser (hydraulic circuitry and tanks, refrigerating and gasification units, sanitization elements), which do not require in-depth treatment as they are part of known technique in the sector.

The dispenser 10 comprises a user interface 112, for example a touch screen, for managing its operation and providing operating instructions to the user.

Figure 2:
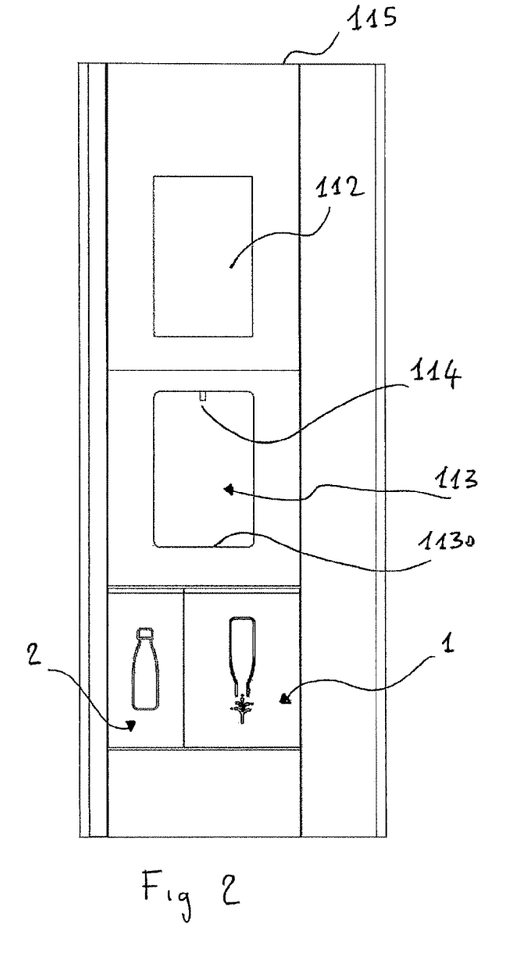
FIG. 2 is a front view of a detail of the dispenser of FIG. 1.

As per known technique, dispenser 10 then comprises a dispensing station 113 (hereinafter referred to as "dispensing compartment 113"), comprising a support surface 1130 for a container 9 and at least one nozzle 114 for dispensing the beverage, positioned above said support surface 1130.

Said support surface 1130 of said dispensing compartment 113 is preferably provided with a grate for draining the beverage possibly coming out of the container 9 or dripping from the dispensing nozzle 114.

Figure 3:
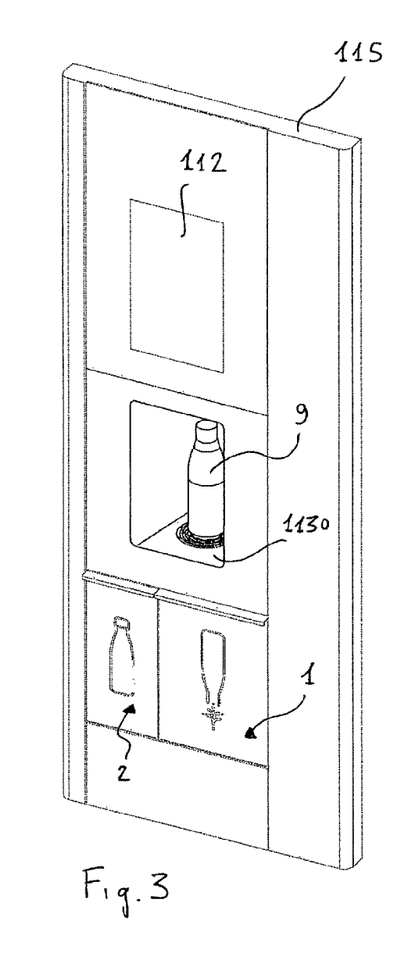
FIG. 3 is a perspective view of as shown in FIG. 2, which shows the container located in the beverage dispensing compartment.

In the example of the figures annexed, this container 9 consists of a bottle or flask. However, obviously, as described herein applies to any container having a shape and size such as to be placed in the dispensing compartment 113 and in the washing compartment 1, which will be briefly described herein.

In fact, dispenser 10 comprises a washing compartment 1 for a container 9, in particular for a container 9 substantially and/or essentially having the shape of a bottle.

An example of a dispenser provided with a washing compartment for a container is shown in the prior document WO94/06547.

The dispenser 10 comprises a first basket 11 (or washing basket 11), adapted to contain the container 9 to be washed inside said washing compartment 1.

The basket 11 is movable between a first operating position and a second operating position.

In the first operating position (shown in FIGS. 1, 2 and 3), the basket 11 is completely inserted into the washing compartment 1 to allow carrying out the washing operations of the container 9 contained therein.

In this first operating position, the basket 11 is designed to receive the container 9 in an inverted position, i.e. with the neck facing downwards and the bottom facing upwards.

In the second operating position (shown in FIG. 4), the basket 11 protrudes, at least partially, from the washing compartment 1, to allow the container 9 to be washed to be inserted and extracted once the washing operations have been completed.

Figure 4:
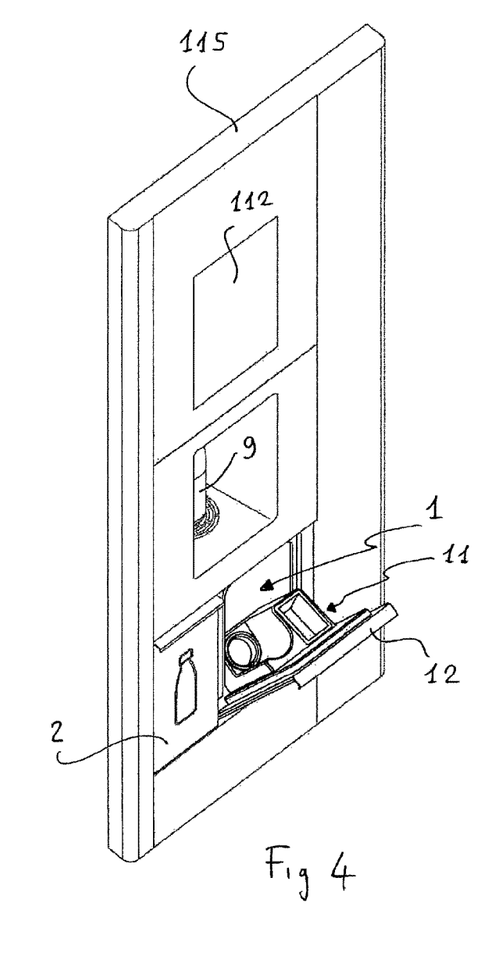
FIG. 4 is a perspective view of the same detail of FIGS. 2 and 3, which shows a first door open to access a washing compartment for a container.

The basket 11 is integral with a closing door 12, the actuation of which allows to move said basket 11 between the first and the second operating position.

The dispenser 10 comprises a washing device, further described below, for dispensing one or more washing fluids inside the container 9 inserted in said basket 11, when the latter is in the first operating position, i.e. completely inserted inside the washing compartment 1.

Said washing device is designed to supply, alternatively, filtered water and water plus ozone: more specifically, said washing device is designed to supply in sequence:
- a first fluid consisting in filtered water for the execution of a pre-washing step inside container 9;
- a second fluid consisting in water plus ozone for sanitization step inside said container 9;
- a third fluid consisting in filtered water for the execution of a rinsing step inside container 9.

As described above becomes clearer with the aid of FIGS. 7, 8 and 9, which show the conformation of the basket 11 and of the relative washing device.

Figure 7:
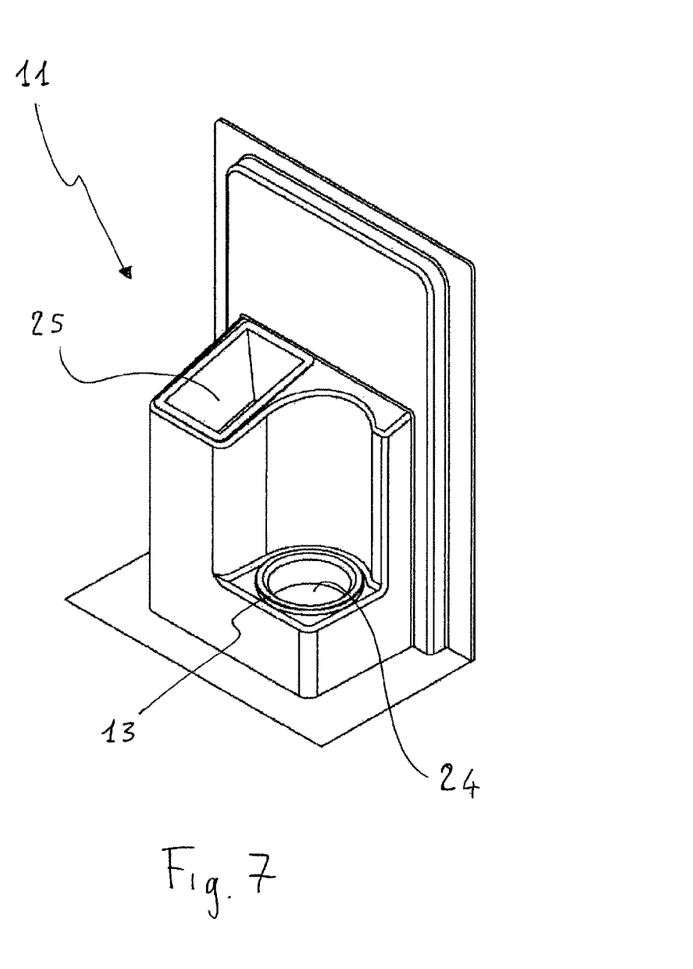
FIG. 7 is a perspective view of a basket designed to receive a container and a cap that must be washed and sanitized.
Figure 8:
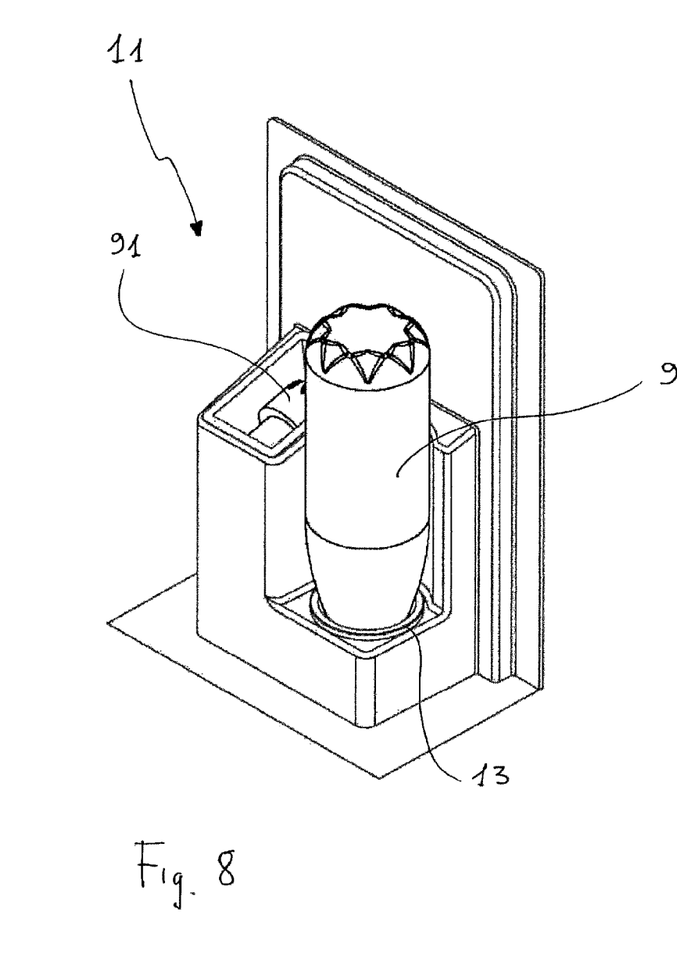
FIG. 8 is the same view of FIG. 7 showing the container and the cap placed in position inside the basket to be washed and sanitized.

In the example illustrated, the basket 11 is shaped in such a way as to provide a self-centring seat 24 designed to couple with the neck of the container 9, inserted in an inverted position.

Said self-centring seat 24 for the container 9 comprises a collar 13 which, in addition to being a centring element for the neck of the container 9, also acts as a hydraulic seal against any splashes of the washing fluids dispensed by the washing device: in other words, said collar 13 prevents the upper external part of the container 9 (i.e. the portion of the container 9 located above the collar 13) from being wetted by said washing fluids.

Figure 9:
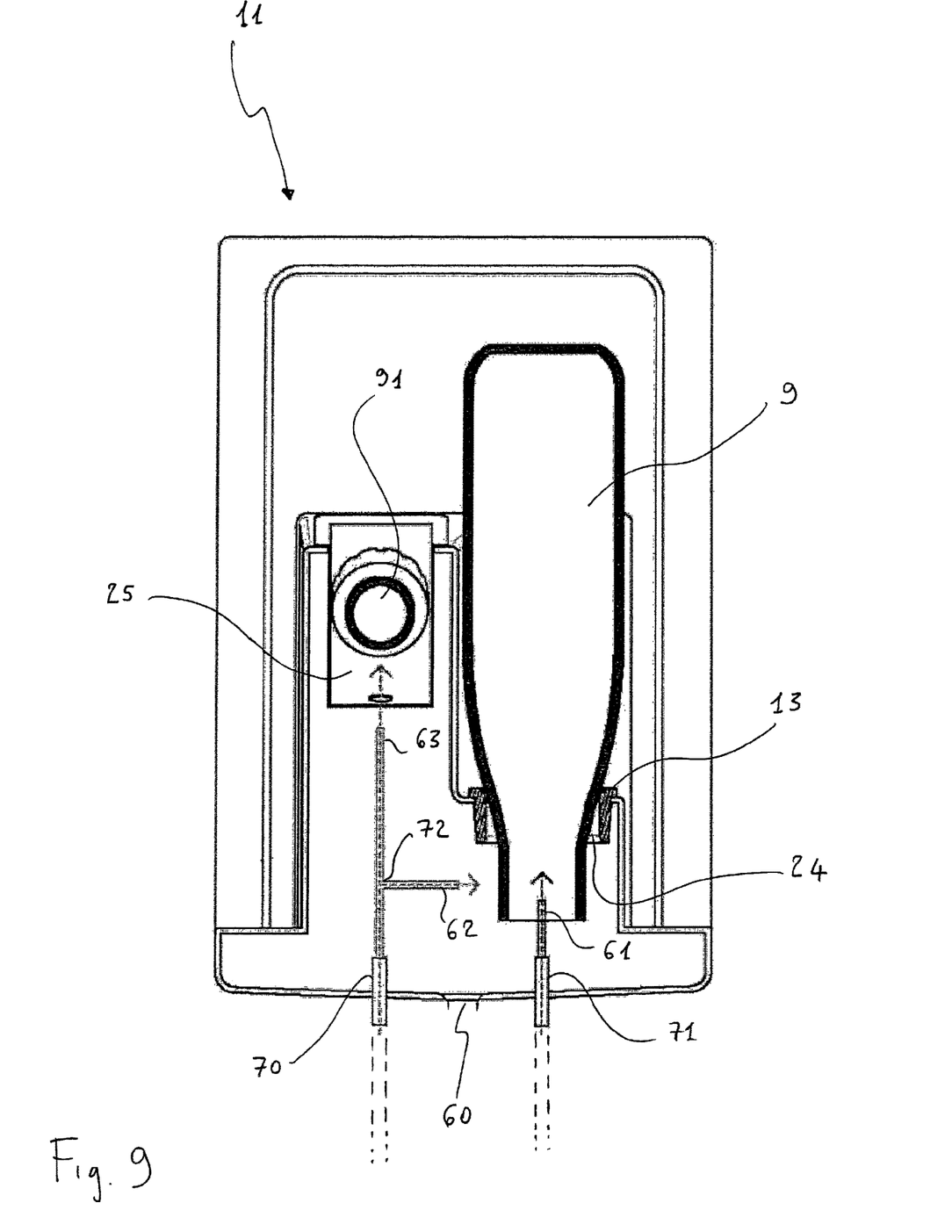
FIG. 9 is a schematic sectional view of the basket of FIG. 8.

As shown in FIG. 9, the said washing device comprises a first nozzle 61 positioned so as to dispense said washing fluids through jets directed upwards inside container 9 inserted with upside down setup in said self-centring seat 24. Said first nozzle 61 comprises an outflow conduit 71, in fluid communication with suitable components not shown in the figure and located inside the dispenser 10, such as a pump for supplying pressurized water and an ozone generator.

The washing fluids dispensed by the first nozzle 61 of the washing device then escape, by gravity, from the mouth of the neck of the container 9, placed in an inverted position, and flow out of the washing compartment 1 through a drain 60 made on the bottom of the basket 11.

In the example illustrated, the basket 11 is further provided with a second seat 25 designed to receive a cap 91 (for example a screw cap or a pressure cap) of the container 9 located in the self-centring seat 24.

The washing device comprises a second nozzle 63 dispensing a fluid inside said second seat 25, said fluid consisting of gaseous ozone supplied through an outflow conduit 70 in fluid communication with an ozone generator: said ozone generator can consist in the same generator used to supply ozone to be added to the water dispensed by the first nozzle 61 inside the container 9; alternatively, a second ozone generator can be provided, specifically connected to the outflow conduit 70 of said second nozzle 63.

Said outflow conduit 70 also comprises a fitting 72 for a third nozzle 62, positioned so as to dispense gaseous ozone outwards of the neck of container 9.

Therefore, the outflow conduit 70 directs a part of the gaseous ozone fluid towards the seat 25 designed to receive the cap 91 (through the second nozzle 63) and a part of the gaseous ozone fluid on the neck of the container 9, below the self-centring seat 24 (through the third nozzle 62, connected to said outflow conduit through the aforementioned fitting 72).

It is noted that the dispensing of gaseous ozone through the second nozzle 63 towards the seat 25 can also occur in the event that the user does not place any cap 91 inside it, given the high volatility of this gas (intended to disperse into the environment as soon as the basket 11 is opened through the closing door 12); the dispensing of gaseous ozone even in the absence of the cap 91 located in the seat also allows saturating the upper portion of the basket 11 with said gas, contributing to the sanitization thereof and of the external portion of the container 9 located above the collar 13 of the self-centring seat 24.

Figure 6:
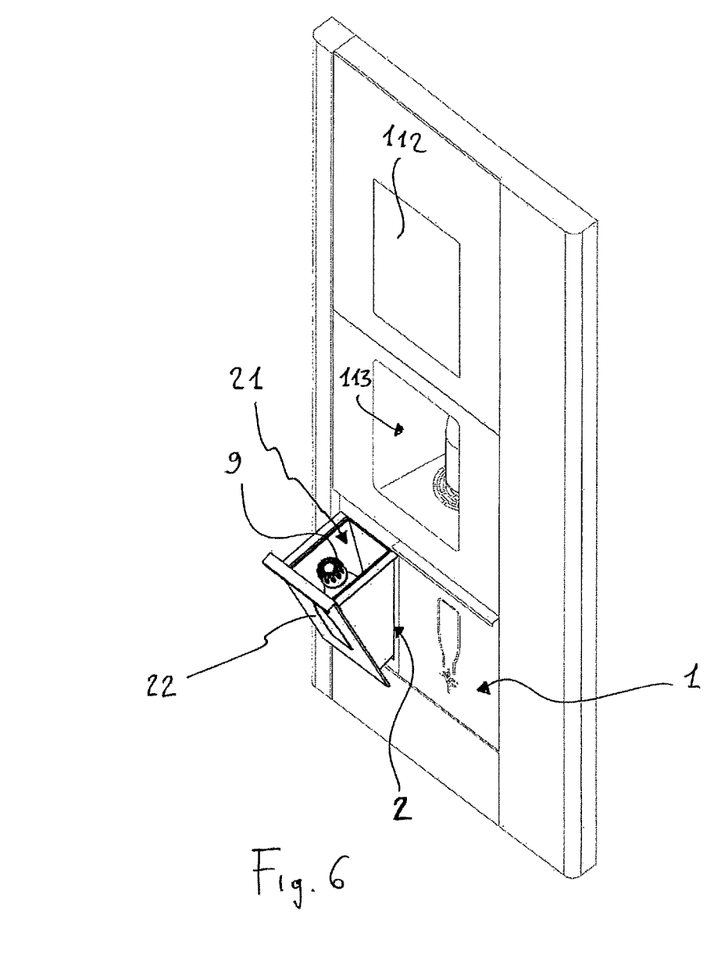
FIG. 6 is a perspective view of the same detail of FIGS. 2, 3 and 4, which shows a second door open, to access a compartment for drawing a container.

In the example illustrated, the dispenser 10 further comprises a drawing compartment 2 for the supply and drawing of a new container 9, substantially and/or essentially having the shape of a bottle.

The dispenser 10 comprises a second basket 21 (or drawing basket 21) designed to receive said new container 9 inside said drawing compartment 2. The basket 21 is movable between a first operating position, in which it is completely inserted in the drawing compartment 2, and a second operating position, in which it at least partially protrudes from said drawing compartment 2 to allow the user to draw the container 9 contained therein.

The basket 21 is integral with a closing door 22, the actuation of which allows to move said basket 21 between the first and the second operating position.

Figure 5:
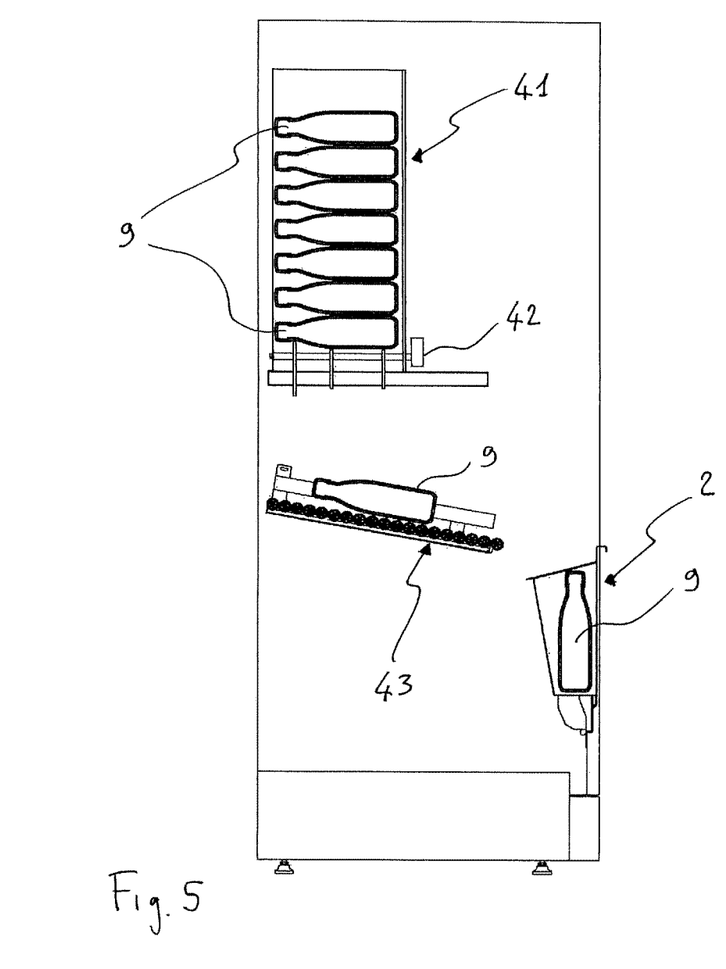
FIG. 5 is a schematic sectional view of the dispenser of FIG. 1.

As shown in FIG. 5, the dispenser 10 comprises a housing area 41 (hereinafter abbreviated to "store 41") inside the cabinet 100, designed to contain a plurality of new containers 9.

A known mechanism 42 is designed to make a container 9 descend at a time from said store 41 towards an underlying slide 43 (in the example illustrated having an idle roller conveyor configuration) to transport it, by gravity, inside the basket 21 of the drawing compartment 2, when said basket 21 is in the first operating position.

Said drawing compartment 2 is used by the user of the dispenser 10 if the user does not already have a container 9 (or similar container designed for the purpose) designed to be placed in the washing compartment 1 for washing and subsequent filling with the selected beverage in the dispensing compartment 113; in other words, if the user already has a similar container, the supply and drawing function of a new container 9 may not be necessary and the functions of the dispenser 10 associated with the drawing compartment 2 will be unused.

In the example illustrated, both the closing door 12 of the basket 11 of the washing compartment 1 and the closing door 22 of the basket 21 of the drawing compartment 2 are tilting doors, which can be operated manually.

Furthermore, the beverage dispensing compartment 113 is located at a lower height than the user interface 112, and the washing compartment 1 and the dispensing compartment 2 are located at a lower height than said dispensing compartment 113.

This combination of solutions is very useful for the ease of use of the dispenser 10 by the user, allowing to use its functions in accordance with ergonomic principles, without particular stress for the musculoskeletal system or the need for bending the legs for using the washing compartment 1 and for drawing a new container 9 from the dispensing compartment 2.

In the example illustrated, the cabinet 100 of the dispenser 10 comprises an openable door 115 to allow access to its interior and carry out normal maintenance activities, such as for example the supply of new containers 9 in the store 41 or the maintenance of the various constructive-functional components.

In this form of realization, the washing compartment 1, drawing compartment 2, dispensing compartment 113 and user interface 112 are positioned on said openable door 115.

From the above description, the advantages that can be achieved with this invention with respect to the solutions of known technique appear clear, both in terms of functionality and practicality of use.

It is clear that numerous variants to dispenser 10 described above are possible for skilled experts, without thereby departing from the areas of innovation inherent in the inventive idea, as it is clear that in the practical implementation of the finding, the various components previously described may be replaced by technically equivalent elements.

For example, it is possible to provide a variant of the dispenser 10 in which the dispensing compartment 113 has the features protected by the patent EP3049364 owned by the same applicant, i.e. with a system comprising a coupling between reciprocal centring elements between said dispensing compartment 113 and the container 9, said coupling activating a wireless communication system for the exchange of data between the container 9 and the dispenser 10 through dialogue and reading means located on said reciprocal centring elements.

A variant of the dispenser 10 can also be provided in which the basket 11 of the washing compartment 1, in addition to the washing device of the example illustrated, comprises one or more bactericidal means (such as, for example, UV lamps), positioned on the upper portion of said washing compartment 1 or on the side walls of the basket 11, so as to contribute to further sanitizing the cap 91 and the outside of the container 9.

The invention claimed is:

1. Dispenser, for the dispensing of drinking water and/or other beverages, comprising:
    a cabinet having a support base and a top;
    a user interface;
    a dispensing compartment having a support surface for a container to be filled;
    at least one nozzle for the dispensing of drinking water and/or other beverages, positioned over said support surface;
    a washing compartment for said container, said washing compartment comprising:
        a washing device for dispensing one or more washing fluids inside said container,
        a drain for draining one or more washing fluids outside said washing compartment,
    wherein
    said washing compartment for said container further comprises
    a basket adapted to contain said container to be washed in an upside down orientation, said basket being movable between:
        a first operating position, wherein it is completely inserted inside said washing compartment to enable to wash the container contained therein,
        and a second operating position, wherein it projects, at least partially, from said washing compartment to enable to insert said container to be washed and pull it out once the washing operations are concluded,
    said washing device being adapted to provide, sequentially, water and water plus ozone, when said basket is located in said first operating position.

2. Dispenser, according to claim 1, wherein
    said basket of said washing compartment comprises a self-centring seat provided with a collar adapted to couple with the neck of a container inserted with upside down orientation,
    and wherein said washing device comprises a first nozzle positioned so as to dispense said one or more washing fluids through jets directed upwards inside said container inserted with upside down orientation in said self-centring seat.

3. Dispenser according to claim 2, wherein
    said one or more washing fluids dispensed by said first nozzle comprise filtered water and water plus ozone.

4. Dispenser according to claim 3, wherein
    said first nozzle dispenses in sequence:
        a first fluid consisting in filtered water for the execution of a pre-washing step inside said container;
        a second fluid consisting in water plus ozone for the execution of a rinsing step inside said container;
        a third fluid consisting in filtered water for the execution of a rinsing step inside said container.

5. Dispenser according to claim 2, to wherein
    said first nozzle comprises an outflow conduit in fluid communication with a pump and an ozone generator.

6. Dispenser according to claim 1, wherein
    said basket is further equipped with a second seat adapted to accommodate a cap for said container located in said self-centring seat.

7. Dispenser according to claim 6, wherein
    the washing device comprises a second nozzle adapted to dispense gaseous ozone inside said second seat.

8. Dispenser according to the previous claim 7, wherein
    said second nozzle comprises an outflow conduit in fluid communication with an ozone generator.

9. Dispenser according to claim 8, wherein
    said outflow conduit comprises a fitting for the third nozzle positioned so as to dispense gaseous ozone outwards of the neck of the container located in an upside down orientation in the self-centring seat (24).

10. Dispenser according to claim 1, comprising
    a compartment configured for drawing a new container, said compartment comprising:
        a basket adapted to receive said new container, said basket being movable between a first operating position, wherein it is inserted inside said compartment in order to be able to receive said new container, and a second operating position, wherein it comes out, at least partially, from said compartment to enable to draw said new container contained therein;
        a store for a plurality of said new containers, comprising a mechanism for bringing, through a slide, a new container at a time inside said basket of said compartment, when said basket is in said first operating position.

11. Dispenser according to claim 10, wherein
    said basket of said washing compartment and said basket of said compartment for drawing a new container are integral to respective closing doors, the operation thereof enables said baskets to be moved between said first and second operating position.

12. Dispenser according to claim 11, wherein
    said closing doors are manually operable, pivoting doors.

13. Dispenser according to claim 10, wherein
said cabinet comprises an openable door to allow accessing therein, and wherein said washing compartment, drawing compartment, dispensing compartment and user interface are positioned on said openable door.

14. Dispenser according to any previous claim 13, wherein
said dispensing compartment and said container comprise respective centring means, the coupling of said reciprocal centring means activating a wireless communication system for the exchange of data between said dispenser and said container, through dialogue and reading means located on such reciprocal centring means.

15. Dispenser according to claim 1, wherein
the basket of the washing compartment comprises one or more bactericidal means positioned on the upper portion of said washing compartment or on the side walls of said basket.

\* \* \* \* \*